(12) United States Patent
Sankai

(10) Patent No.: US 11,746,316 B2
(45) Date of Patent: Sep. 5, 2023

(54) THREE-DIMENSIONAL STRUCTURING METHOD AND THREE-DIMENSIONAL STRUCTURING SYSTEM OF CELLS

(71) Applicants: CYBERDYNE Inc., Tsukuba (JP); University of Tsukuba, Tsukuba (JP)

(72) Inventor: Yoshiyuki Sankai, Ibaraki (JP)

(73) Assignees: CYBERDYNE Inc., Tsukuba (JP); University of Tsukuba, Tsukuba (JP)

( * ) Notice: Subject to any disclaimer, the term of this patent is extended or adjusted under 35 U.S.C. 154(b) by 1128 days.

(21) Appl. No.: 16/324,496

(22) PCT Filed: Jun. 9, 2017

(86) PCT No.: PCT/JP2017/021552
§ 371 (c)(1),
(2) Date: Feb. 8, 2019

(87) PCT Pub. No.: WO2018/029970
PCT Pub. Date: Feb. 15, 2018

(65) Prior Publication Data
US 2019/0169558 A1    Jun. 6, 2019

(30) Foreign Application Priority Data
Aug. 10, 2016    (JP) .................................. 2016-158063

(51) Int. Cl.
*C12M 1/12*    (2006.01)
*C12M 1/34*    (2006.01)
(Continued)

(52) U.S. Cl.
CPC .............. *C12M 25/12* (2013.01); *C12M 3/00* (2013.01); *C12M 21/08* (2013.01); *C12M 25/02* (2013.01);
(Continued)

(58) Field of Classification Search
CPC ........ C12M 25/12; C12M 3/00; C12M 21/08; C12M 25/02; C12M 27/16; C12M 29/10;
(Continued)

(56) References Cited

U.S. PATENT DOCUMENTS 5,026,365 A * 6/1991 Rossini ............... A61M 1/3689
424/93.71
5,595,909 A * 1/1997 Hu ....................... A61M 1/1625
435/182
(Continued)

FOREIGN PATENT DOCUMENTS

| EP | 1367119 A2 | 2/2001 |
| EP | 1078982 A2 | 3/2003 |

(Continued)

OTHER PUBLICATIONS

Chapman, L. A. C., et al., Optimising Cell Aggregate Expansion in a Perfused Hollow Fibre Bioreactor via Mathematical Modelling, PLOS One, Aug. 2014, 9(8), e105813, 14 pgs.
(Continued)

*Primary Examiner* — Liban M Hassan
(74) *Attorney, Agent, or Firm* — Procopio, Cory, Hargreaves & Savitch LLP

(57) ABSTRACT

Proposed are a three-dimensional structuring method of cells and a three-dimensional structuring system of cells capable of efficiently bonding multiple cell clusters in a three-dimensional direction, pursuant to their growth, while ensuring safety. A plurality of fibers, in which one end of each of the fibers is held by a flat plate, are inserted together with the flat plate into a flow path through which a culture solution is supplied, a plurality of cell clusters are placed in the flow path upon causing the cell clusters to run with a liquid flow of the culture solution, and each of the cell clusters is (Continued)

cultured by being stacked on an outer surface of each of the fibers with the flat plate as a growth origin.

5 Claims, 17 Drawing Sheets

(51) Int. Cl.
    *C12M 1/36* (2006.01)
    *C12M 3/06* (2006.01)
    *C12N 5/077* (2010.01)
    *C12M 3/00* (2006.01)
    *C12N 5/00* (2006.01)
    *C12M 1/00* (2006.01)

(52) U.S. Cl.
    CPC ............ *C12M 27/16* (2013.01); *C12M 29/10* (2013.01); *C12M 29/16* (2013.01); *C12M 41/14* (2013.01); *C12M 41/34* (2013.01); *C12M 41/44* (2013.01); *C12M 41/48* (2013.01); *C12N 5/00* (2013.01); *C12N 5/0658* (2013.01)

(58) Field of Classification Search
    CPC ...... C12M 29/16; C12M 41/14; C12M 41/34; C12M 41/44; C12M 41/48; C12M 25/10; C12M 25/14; C12N 5/00; C12N 5/0658; C12N 5/0062
    See application file for complete search history.

(56) References Cited

U.S. PATENT DOCUMENTS

| | | | | |
|---|---|---|---|---|
| 5,605,835 A | * | 2/1997 | Hu | .................... C12M 29/16 435/297.2 |
| 7,160,719 B2 | * | 1/2007 | Nyberg | ............... A61M 1/3489 435/325 |
| 2003/0224510 A1 | * | 12/2003 | Yamaguchi | ............ C12M 21/08 435/292.1 |
| 2011/0200559 A1 | | 8/2011 | Koga et al. | |
| 2013/0337553 A1 | | 12/2013 | Nakayama | |
| 2014/0073034 A1 | * | 3/2014 | Page | ........................ C12Q 1/24 435/308.1 |

FOREIGN PATENT DOCUMENTS

| | | | | |
|---|---|---|---|---|
| JP | 2004283010 A | * | 10/2004 | ............ C12M 21/08 |
| JP | 4517125 B2 | | 8/2010 | |
| JP | 2011-172533 A | | 9/2011 | |
| JP | 5769334 B2 | | 8/2015 | |
| JP | 2016-77229 A | | 5/2016 | |

OTHER PUBLICATIONS

De Napoli, I. E. et al., Mesenchymal Stem Cell Culture in Convection-Enhanced Hollow Fibre Membrane Bioreactors for Bone Tissue Engineering, Journal of Membrane Science, 2011, 379, pp. 341-352.

Kazutomo, B., et al., Development of Biomimetic System for Scale up of Cell Spheroids—Building Blocks for Cell Transplantation, 2017 39th Annual International Conference of the IEEE Engineering in Medicine and Biology Society (EMBC), Jul. 11, 2017, pp. 1611-1616.

Extended European Search Report for related EP App No. 17839045.6 dated Feb. 7, 2020, 9 pgs.

Eghbali, H. et al., "Hollow Fiber Bioreactor Technology for Tissue Engineering Application" Int. J. Artif. Organs, Feb. 2016, 16 pages; vol. 39, No. 1.

International Search Report and Written Opinion for related International Application No. PCT/JP2017/021552, dated Aug. 8, 2017; English translation of ISR provided; 6 pages.

\* cited by examiner

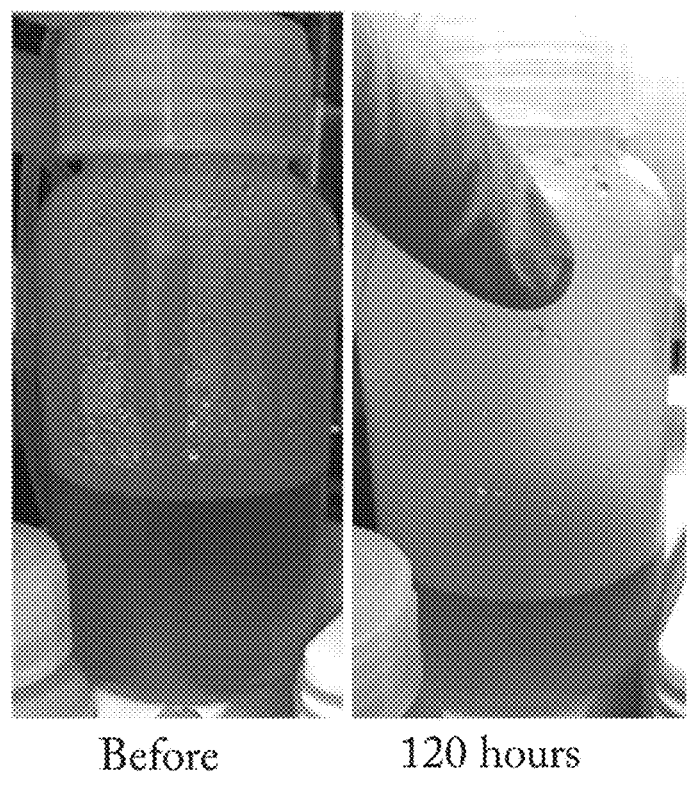
Before    120 hours
*FIG.14A*    *FIG.14B*

Before 120 hours

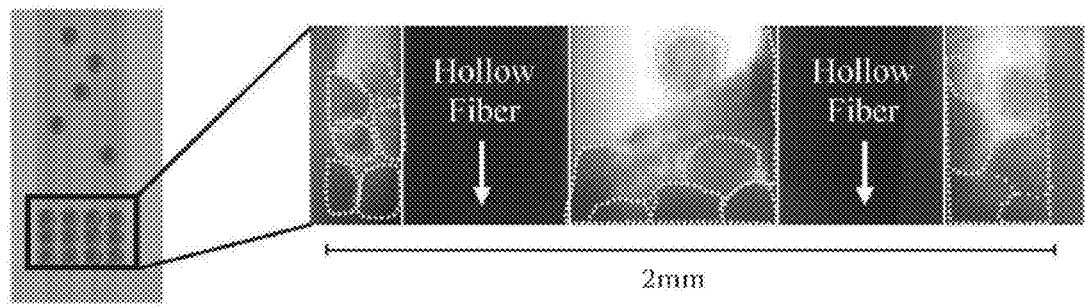
*FIG.16A*          *FIG.16B*

THREE-DIMENSIONAL STRUCTURING METHOD AND THREE-DIMENSIONAL STRUCTURING SYSTEM OF CELLS

CROSS-REFERENCE TO RELATED APPLICATIONS

This application is a U.S. National Stage entry of PCT Application No: PCT/JP2017/021552 filed Jun. 9, 2017, which claims priority to Japanese Patent Application No. 2016-158063, filed Aug. 10, 2016, the contents of which are incorporated herein by reference.

TECHNICAL FIELD

The present invention relates to a three-dimensional structuring method of cells and a three-dimensional structuring system of cells, and in particular can be suitably applied to the culture method and culture system of cell clusters in which nerve cells are stacked and cultured in an intended direction.

BACKGROUND ART

A spinal cord damage causes a severe motility disorder, and considerably deteriorates the QOL (Quality of Life) of patients. Once the central nervous system, such as the brain and spinal cord, is damaged, it is generally said that unaided regeneration is impossible.

In the regenerative medicine area in recent years, while a treatment technique of building cell tissues, which become the basis of nerve tissues, ex vivo and transplanting the built cell tissues for improving and regenerating the functions of patients has been devised, the current situation is that a method of building cell tissues themselves has not yet been established. In particular, it is said that the formation of a three-dimensional structure of cells is important in building nerve cell tissues for functional improvement and regeneration.

Nevertheless, because the formation of a three-dimensional structure of cells depends on the growth direction of cells and is difficult to control artificially, the development of a technique for arbitrarily building a three-dimensional structure of cells is required.

Conventionally, while methods of stacking cell clusters, which are spherical aggregations of cells, one cell cluster at a time have been developed, an enormous amount of time is required for the three-dimensional structuring of cells, and the current state is that it is difficult to move ahead with the research area related to the three-dimensional structuring of nerve cells.

In recent years, as a method of three-dimensionally structuring a plurality of cell clusters, proposed is a method of placing cell clusters, which are supplied from an open end side of a bottomed cylindrical transplantation guide, on a bottom material, and immersing the bottom material side in an excessive amount of culture solution to cultivate the cell clusters and forming a three-dimensional structure of cells (refer to PTL 1).

Moreover, proposed is a method of accumulating cell clusters by penetrating the cell clusters with needle-shaped bodies, and causing the cell clusters to come into contact with each other between adjacent needle-shaped bodies to prepare a three-dimensional structure (refer to PTL 2). Furthermore, proposed is a method of coating a surface of a core shell-type fibrous base material with cell layers and forming a stack (refer to PTL 3).

CITATION LIST

Patent Literature

[PTL 1] Japanese Patent Registration No. 5769334
[PTL 2] Japanese Patent Registration No. 4517125
[PTL 3] Japanese Unexamined Patent Publication Application No. 2016-77229

SUMMARY OF THE INVENTION

Problems to be Solved by the Invention

Meanwhile, PTL 1 merely molds a cylindrical transplantation guide, and, in addition to the problem that the anchorage in the stacking direction becomes unstable based on equalization by gravity, there is also an uncertainty in that the respective cell clusters may not grow sufficiently merely by immersing growth factors or nutritional factors in a culture medium.

Moreover, with PTL 2, when the needle-shaped body as the anchorage is to be pulled out from a plurality of stacked cell clusters, there is a problem in that the respective cell clusters are likely to become damaged. While there will be no problem if each cell cluster is configured from relatively strong cells of cartilage or the like, with delicate cells such as nerve cells, there is a problem in that the cell clusters may rupture when the needle is pulled out.

Furthermore, PTL 3 describes a method of stacking cell clusters in a hollow part of the fiber base material, while causing the cell clusters to flow together with the culture solution, in consideration of the mechanical strength, but there is a problem in that the efficiency will deteriorate because additional steps of removing the gel of the core part and hollowing the inside of the fiber base material become required.

The present invention was devised in consideration of the foregoing points, and proposes a three-dimensional structuring method of cells and a three-dimensional structuring system of cells capable of efficiently bonding multiple cell clusters in a three-dimensional direction, pursuant to their growth, while ensuring safety.

Means to Solve the Problems

In order to achieve the foregoing object, the present invention provides a three-dimensional structuring method of cells comprising the steps of positioning a plurality of fibers in a flow path spatial part, in which a space surrounded by an inner wall surface from a supply port to a discharge port of a culture solution is used as a flow path, so that a longitudinal direction of each of the fibers is along a direction of the flow path while a predetermined interval is mutually maintained between the fibers, and placing a plurality of cell clusters in the flow path upon causing the cell clusters to run with a liquid flow of the culture solution supplied in the flow path from the supply port, and culturing each of the cell clusters by stacking the cell clusters on an outer surface of each of the fibers with a vicinity of the discharge port as a growth origin.

Because a plurality of cell clusters, which are supplied in the flow path upon causing the cell clusters to run with the liquid flow of the culture solution, are stacked along a flow path direction while being attached to the outer surface of each fiber with the vicinity of the discharge port as the growth origin, it is possible to efficiently form a three-dimensional structure of bonded cells while growing the cell clusters in a three-dimensional direction without damaging the cell clusters.

Moreover, the three-dimensional structuring system of cells according to the present invention comprises a flow path spatial part in which a space surrounded by an inner wall surface from a supply port to a discharge port of a culture solution is used as a flow path, a plurality of fibers which are positioned so that a longitudinal direction of each of the fibers is along a direction of the flow path while a predetermined interval is mutually maintained between the fibers, and a liquid supplying part which supplies the culture solution in the flow path from the supply port of the flow path spatial part, wherein a plurality of cell clusters are placed in the flow path upon causing the cell clusters to run with a liquid flow of the culture solution supplied in the flow path from the supply port, and each of the cell clusters is cultured by stacking the cell clusters on an outer surface of each of the fibers with a vicinity of the discharge port as a growth origin.

By continuously supplying a plurality of cell clusters in the flow path upon causing the cell clusters to run with the liquid flow of the culture solution while perfusing the culture solution from this kind of liquid supplying part to the open end of the cylindrical part, these plurality of cell clusters are stacked along a flow path direction while being attached to the outer surface of each fiber with the vicinity of the discharge port as the growth origin. Therefore, it is possible to efficiently form a three-dimensional structure of bonded cells while growing the cell clusters in a three-dimensional direction without damaging the cell clusters.

Furthermore, in the present invention, each of the fibers has a hollow or a lateral groove along a longitudinal direction formed therein, has a plurality of micropores that penetrate from the outer surface to the hollow interior or the lateral groove interior, and metabolic waste is removed from each of the cell clusters through each of the micropores.

By filtering and discharging the metabolic waste of the waste clusters, which flow in from the fiber surface, through the multiple micropores formed on each of the fibers, it is possible to promote the growth of each cell cluster and simultaneously improve the purity of the three-dimensional structure of cells in proportion to the amount of impurities that are eliminated.

Furthermore, in the present invention, each of the fibers supplies either or both of growth factors and nutritional factors to each of the cell clusters through each of the micropores.

By supplying growth factors and nutritional factors to each of the clusters accumulated on the outer surface of the fibers through the multiple micropores formed on each of the fibers, it is possible to efficiently promote the growth of each cell cluster.

Furthermore, in the present invention, the flow rate of the culture solution is controlled, and the number of cell clusters to be placed in the flow path and the placement timing thereof are adjusted in accordance with the control state of the culture solution. Furthermore, at least one or more among a temperature, a carbon dioxide concentration, an oxygen concentration and a nitrogen concentration of the culture solution are controlled.

Consequently, because it is possible to place a plurality of cell clusters in the flow path upon causing the cell clusters to run with the liquid flow of the culture solution while constantly maintaining the culture solution in a state that is close to a physiological environment, it is possible to sufficiently contribute to optimizing the growth of the cell clusters.

Furthermore, in the present invention, subtle vibration is applied to each of the fibers, along a flow path direction, at a predetermined timing in accordance with a growth process of each of the cell clusters. It is thereby possible to prevent each cell cluster which is contacting the outer surface of the fiber from entering each micropore formed in the fiber and making it difficult to slide in the flow path direction. It is thereby possible to remove the grown cell clusters from the fibers relatively easily.

Furthermore, in the present invention, the flow path spatial part is a closed space formed within a ring of an annular seal member by bonding a first case and a second case, in which grooves of a predetermined shape are formed on either or both of opposing surfaces, by interposing the seal member so as to surround the grooves. It is thereby possible to prevent the occurrence of contamination (microbiological contamination) from an external environment during the cell culture.

Furthermore, in the present invention, with each of the fibers, the supply port side is blocked and the discharge port side is opened in the flow path spatial part. Consequently, when the culture solution enters from the supply port of the flow path spatial part, it is possible to discharge the metabolic substance in the culture solution to the discharge port because the discharge port side of each fiber becomes a negative pressure.

Furthermore, in the present invention, each of the fibers is supported in the flow path spatial part so that tensile force is applied between the blocked side and the open side. Consequently, because either end of each fiber is fixed and tensile force is applied along the flow path direction continuously, it is possible to prevent the deflection of each fiber.

Advantageous Effects of the Invention

According to the present invention, it is possible to realize a three-dimensional structuring method of cells and a three-dimensional structuring system of cells capable of efficiently and simultaneously culturing multiple cell clusters and bonding them in a three-dimensional direction, pursuant to their growth, without damaging the cell clusters and while ensuring safety.

BRIEF DESCRIPTION OF DRAWINGS

FIGS. 14A and 14B are diagrams showing the results before and after the contamination test according to the second embodiment.

FIGS. 16A and 16B are diagrams showing the observation after 24 hours of the spheroid dissemination experiment according to the second embodiment.

DESCRIPTION OF EMBODIMENTS

An embodiment of the present invention is now explained in detail with reference to the appended drawings.

(1) Cell Cluster and Three-Dimensional Structuring Method Thereof According to the Present Invention Because anchorage-dependent cells among cells die in a state of floating in the culture solution, it is necessary to attach the cells to the anchorage and proliferate the cells. Cells of skin and bone bond with each other in search of the anchorage during culturing, and cells, and the extracellular matrix produced by the cells themselves, form a cell cluster (spheroid), which is an aggregate. A cell cluster is a spherical aggregate having a diameter of roughly 100 to 400 [μm] formed based on the accumulation of cells, and, when the cell clusters themselves become bonded and fused, the result will be an even larger shape.

Cells suitable for a cell cluster are stem cells (ES cells, cord blood-derived cells, undifferentiated mesenchyme stem cells, etc.), somatic cells, undifferentiated cells such as tumor cells, or their differentiated cells. Moreover, because osteoblastic cells, cartilage cells, and adipose cells can be easily subject to differentiation induction from undifferentiated mesenchyme stem cells, they can also be used as their differentiation-induced cells (articular cartilage cells, bone cells, etc.).

The cell clusters of the present invention can be applied mainly to mesodermal tissues as well as tissues of articular cartilage, bone, adipose tissue of breast and the like, ligament, tendon, teeth, auricle, nose and the like, and can also be applied to nearly all adhesion system cells of liver, pancreas, blood vessels, and nerves without limitation to mesodermal tissues.

Moreover, a cell cluster does not necessarily need to be formed as an aggregate of cells of a single type, and, so as long as a cell cluster is formed, a cell cluster may be formed from multiple types of cells. The cell structure of the present invention can also be produced by using this kind of chimeric spheroid.

Note that, as the culture solution, used is a culture solution obtained by adding 10 [vol %] FBS (Fetal bovine serum) to 90 [vol %] of DMEM (Dulbecco's modified eagle's medium) containing general PSN (Penicillin, Streptomycin, Neomycin: all are antibiotics).

With the three-dimensional structuring method of cells in the present invention, a plurality of the foregoing cell clusters (spheroids) are bonded pursuant to their growth while being accumulated in an optimal perfusion culture environment, and the cell clusters are stacked in the flow path direction of the culture solution to perform three-dimensional structuring.

Figure 1:
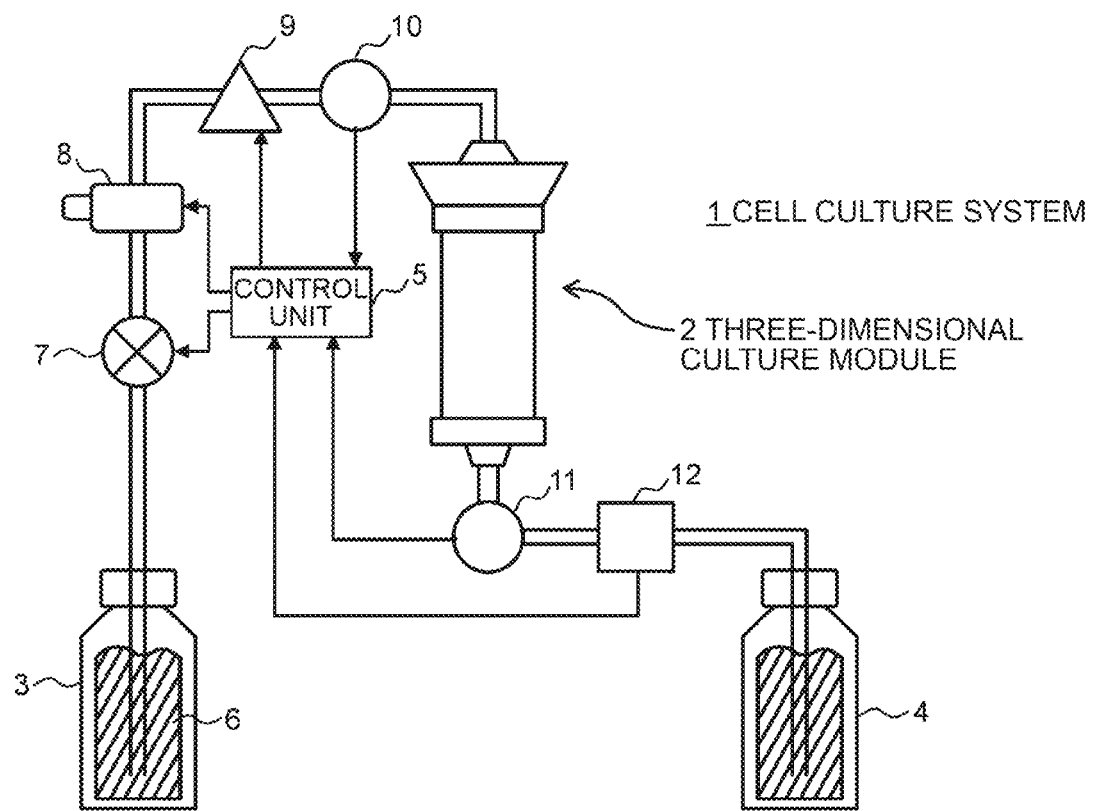
FIG. 1 is a schematic diagram showing the overall configuration of the cell culture system according to the first embodiment of the present invention.

(2) First Embodiment (2-1) Overall Configuration of Cell Culture System in the First Embodiment As shown in FIG. 1, with a cell culture system 1 according to the first embodiment, a culture vessel 3 is connected to an upstream section and a recovery container 4 is connected to a downstream section of a three-dimensional culture module 2, and, under the integrated control of a control unit 5, a culture solution 6 containing growth factors (NGF) and nutritional factors supplied from the culture vessel 3 is perfused to the three-dimensional culture module 2 while maintaining a constant culture environment condition.

With the cell culture system 1, under the control of the control unit 5, the culture solution 6 sucked from the culture vessel 3 with a pump 7 is supplied to the three-dimensional culture module 2 sequentially via a $CO_2$ gas cylinder 8, a heater 9 and a flow rate sensor 10.

A new culture solution 6 is constantly and continuously supplied to the three-dimensional culture module 2, and the cell clusters are sequentially supplied from the outside at a predetermined timing. The three-dimensional culture module 2, as described later, forms a three-dimensional structure of cells by bonding a plurality of cell clusters while stacking them in a flow path direction under circumstances where the culture solution 6 is perfused from the culture vessel 3 to the recovery container 4.

The culture solution 6 discharged from the three-dimensional culture module 2 is transferred to the recovery container 4 sequentially via a temperature sensor 11 and a $CO_2$ sensor 12 on the downstream side.

With the cell culture system 1, the liquid temperature and the concentration of carbon dioxide existing in a solution are controlled so that the culture solution 6 to be supplied to the three-dimensional culture module 2 becomes an optimal culture environment (physiological environment or similar environment) for cell culturing.

In other words, the control unit 5 uses the $CO_2$ gas cylinder 8 to inject carbon dioxide into, and cause the carbon dioxide to exist in, the culture solution 6 while sucking the culture solution 6 from the culture vessel 3 with the pump 7. Here, the control unit 5 controls the pH region of the culture solution 6 to be between 6.8 and 7.2 by maintaining the concentration of the carbon dioxide existing in the culture solution 6 at roughly 5% based on the detection result of the $CO_2$ sensor 12 positioned at the downstream section of the three-dimensional culture module 2.

Moreover, the control unit 5 controls the heater 9 so as to maintain the temperature of the culture solution 6 sucked from the culture vessel 3 at 37° C. based on the detection result of the temperature sensor 11 positioned at the downstream section of the three-dimensional culture module 2.

Furthermore, the control unit 5 drive-controls the pump 7 so as to maintain the flow rate of the culture solution 6 supplied to the three-dimensional culture module 2 at an intended condition.

With the cell culture system 1, as described above, it is possible to constantly supply and perfuse a new culture solution 6 to the three-dimensional culture module 2 from the culture vessel 3 in an environmental condition similar to a physiological environment.

Figure 2:
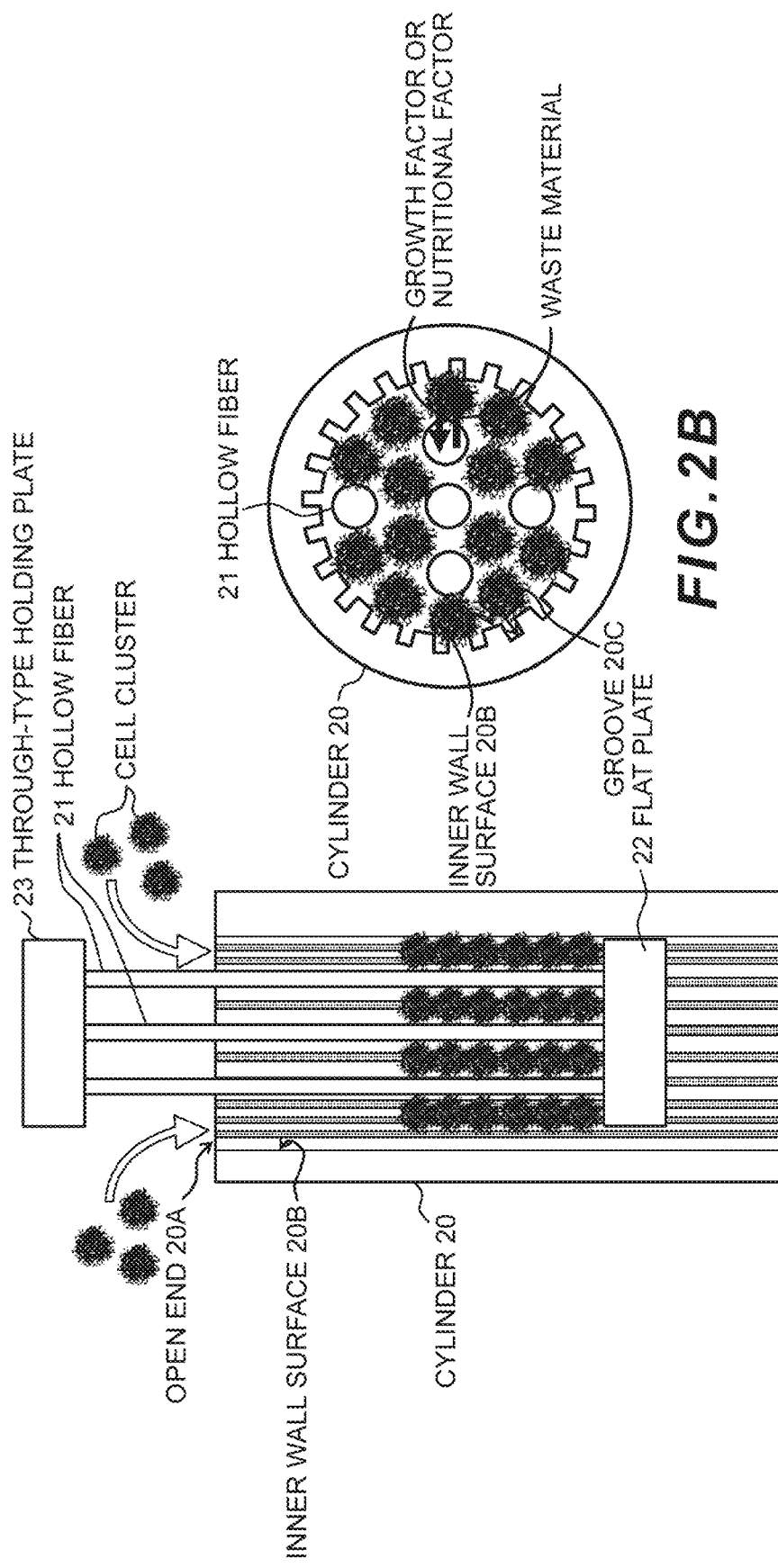
FIGS. 2A and 2B are a schematic cross sections showing the three-dimensional culture module according to the first embodiment.

(2-2) Configuration of Three-Dimensional Culture Module According to the First Embodiment As shown in FIG. 2(A) and FIG. 2(B), the three-dimensional culture module 2 has a cylinder (cylindrical part) 20 in which a space surrounded by an inner wall surface 20B from an open end 20A connected to a supply path of the culture solution 6 is used as a flow path, and a plurality of groove parts 20C are formed on the inner wall surface 20B of the cylinder 20 along the flow path direction.

A flat plate 22 which detachably retains one end of a plurality of hollow fibers 21 is housed in an internal space of the cylinder 20 so that the surface thereof is positioned to maintain a vertical relation relative to the flow path direction of the culture solution 6.

The flat plate 22 is designed to have a shape and size capable of being housed in a cross section shape (flow path width) of the flow path within the cylinder 20, and fitting holes (not shown) corresponding to one end of the plurality of hollow fibers 21 are formed by penetrating the flat plate 22.

The other end of the plurality of hollow fibers 21 is detachably held by a through-type holding plate 23. The through-type holding plate 23 is formed with a plurality of penetration holes corresponding to each of the fitting holes of the flat plate 22. Moreover, the through-type holding plate 23 is designed to have a shape and size capable of being housed in a cross section shape of the flow path within the cylinder 20 as with the flat plate 22.

Upon positioning the flat plate 22 and the through-type holding plate 23 within the cylinder 20 of the three-dimensional culture module 2, the culture solution 6 to be supplied from the open end 20A of the cylinder 20 to the flow path can flow to the downstream section through the plurality of groove parts 20C without the existence of the through-type holding plate 23 and the flat plate 22 becoming a resistance. Here, the culture solution 6 is supplied to the plurality of hollow fibers 21 via each of the penetration holes of the through-type holding plate 23, and it is thereby possible to cause the culture solution 6 flow to the downstream section of the flow path through each of the fitting holes of the flat plate 22.

The plurality of hollow fibers 21 are integrally housed in the internal space of the cylinder 20 in a state of being fixed and held where one end and the other end thereof are sandwiched by the flat plate 22 and the through-type holding plate 23.

Here, with the plurality of hollow fibers 21, because the corresponding hollow interior is communicably connected to the internal space of the cylinder 20 via each of the penetration holes of the through-type holding plate 23 and each of the fitting holes of the corresponding flat plate 22, the culture solution supplied from the open end 20A of the cylinder 20 is discharged to the internal space (flow path) of the cylinder 20 through the hollow interior of each hollow fiber 21.

Figure 3:
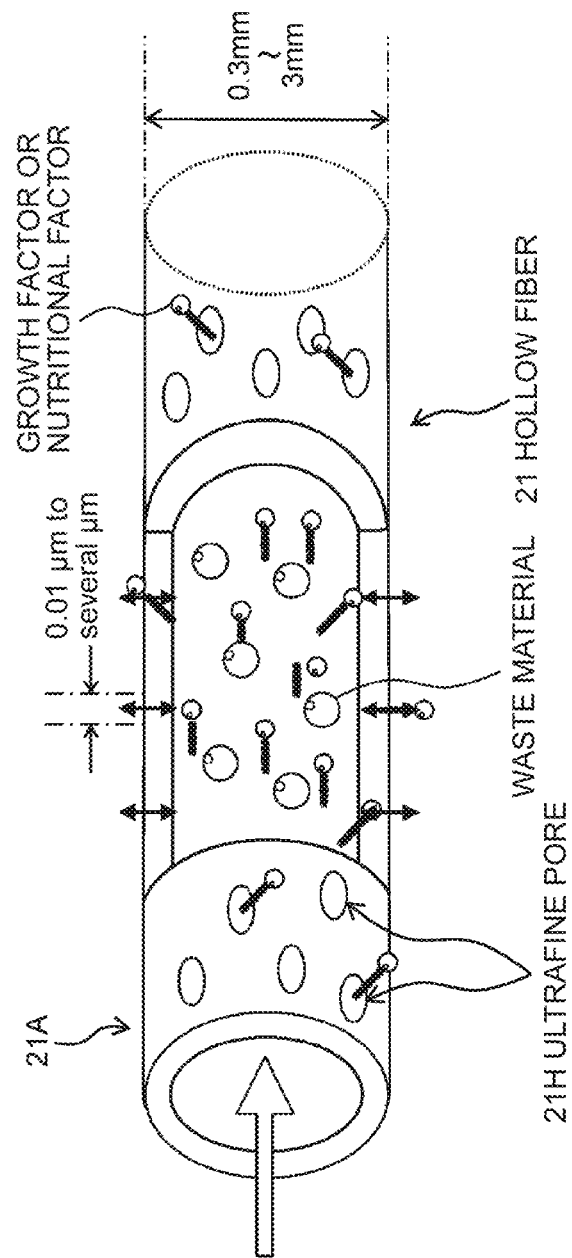
FIG. 3 is a conceptual diagram showing the functional configuration of the hollow fiber according to the first embodiment.

As shown in FIG. 3, each hollow fiber 21 is formed from a filamentous hollow fiber membrane formed using a chemical fiber having a diameter of roughly 0.3 [mm] to 3 [mm], and multiple slit-like ultrafine pores 21H having a pore width of 0.01 [µm] to several [µm] are formed by penetrating the fiber surface (outer surface) 21A.

Consequently, the growth factors (NGF) and nutritional factors in the culture solution can be leaked to the fiber surface 21A through the multiple ultrafine pores 21H formed on each hollow fiber 21, and the waste material and impurity substance of the cell clusters that flow in from the fiber surface 21A can be filtered and discharged.

The arrangement of the plurality of hollow fibers 21 can be freely set, irrespective of whether or not there is a pattern sequence in the internal space of the cylinder 20, so as long as it is possible to maintain spacing capable of sufficiently supplying, at a practical level, the growth factors and nutritional factors to the cell clusters accumulated on the outer surface 21A of the hollow fiber 21.

In other words, this is because, in the process of forming a three-dimensional structure of cells, even at the stage where the cell cluster group accumulated on the outer surface 21A of each hollow fiber 21 is still growing, even if each of the hollow fibers 21 is pulled out from the cell cluster group, the cell clusters become bonded to fill the space where each of the hollow fibers 21 exists pursuant to their subsequent growth so as long as the cell cluster group is continued to be cultured.

Figure 4:
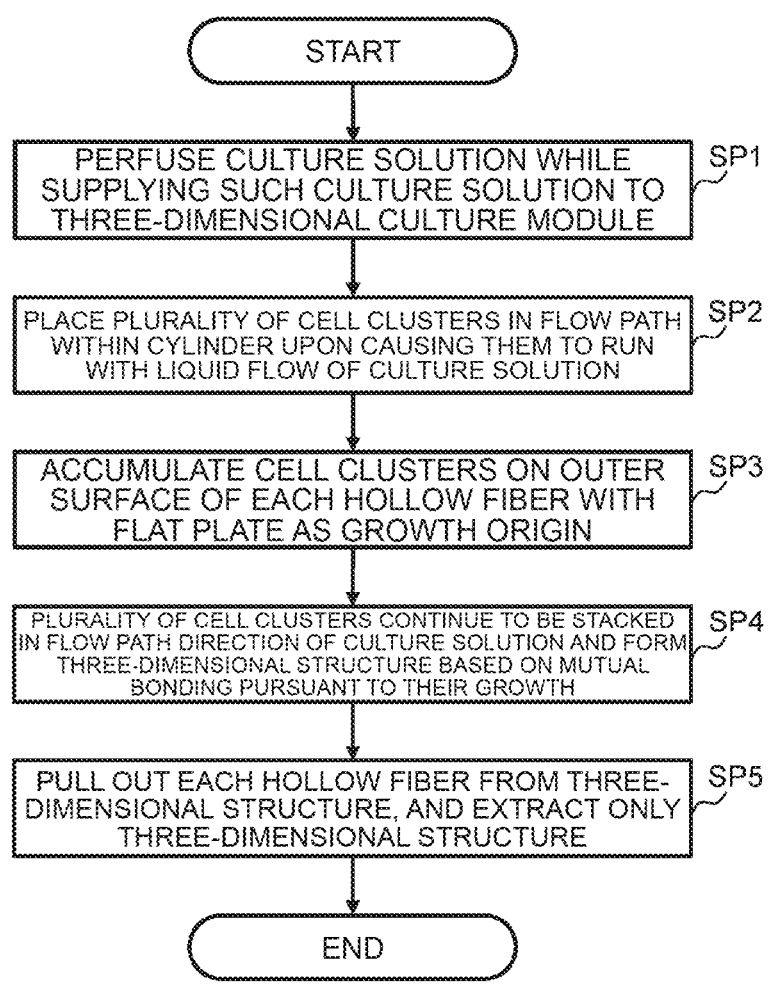
FIG. 4 is a flowchart showing an operational example of the cell culture system according to the first embodiment.

(2-3) Three-Dimensional Structuring Method of Cells According to the First Embodiment FIG. 4 shows a flowchart showing an operational example of the cell culture system 1 according to the first embodiment. Foremost, in the three-dimensional culture module 2, the plurality of hollow fibers 21 that are fixed and held between the through-type holding plate 23 and the flat plate 22 are housed in the internal space (on the flow path) of the cylinder 20.

Next, in the cell culture system 1, the control unit 5 controls the pump 7 and perfuses the culture solution 6 in the culture vessel 3 while supplying the culture solution 6 from the open end 20A of the cylinder 20 of the three-dimensional culture module 2 and maintaining a constant culture environment condition (step SP1).

In a state where a new culture solution 6 is constantly supplied to the flow path in the cylinder 20, a plurality of cell clusters are placed in the flow path from the open end 20A of the cylinder 20 upon causing the cell clusters to run with the liquid flow of the culture solution 6 at the intended timing (step SP2).

The plurality of cell clusters placed within the cylinder 20 start accumulating on the outer surface 21A of each hollow fiber 21 while randomly coming into contact with the surface of the flat plate 22 (step SP3). Next, when the plurality of cell clusters are further placed within the cylinder 20 upon running with the liquid flow of the culture solution 6, they are accumulated on the outer surface 21A of each of the hollow fibers 21 while coming into contact with the cell clusters that have been previously accumulated on the surface of the flat plate 22, and continue to become stacked in the flow path direction.

Here, growth factors or nutritional factors are supplied to the respective cell clusters, which are accumulated on the outer surface 21A, from the hollow interior of each hollow fiber 21 via multiple ultrafine pores, and at the same time metabolic substance and waste material are filtered and discharged to the hollow interior from each of the cell clusters via the multiple ultrafine pores 21H.

Accordingly, in the three-dimensional culture module 2, not only do the adjacent cell clusters grow and bond with each other while a plurality of cell clusters accumulate on the outer surface 21A of each of the hollow fibers 21, the cell clusters stacked along the flow path direction also grow and bond with each other (step SP4).

When the placement of cell clusters in the three-dimensional culture module 2 is eventually completed, a three-dimensional structure in which multiple cell clusters are mutually bonded in a three-dimensional direction is formed in the internal space of the cylinder 20 with the flat plate 22 as the growth origin.

In the three-dimensional culture module 2, after the plurality of hollow fibers 21 are removed from the cylinder 20 together with the flat plate 22 and the through-type holding plate 23, by removing all hollow fibers 21 from the flat plate 22 in the push-pull operation (reciprocating motion in the fiber direction), only the three-dimensional structure of cells will remain on the surface of the flat plate 22 (step SP5).

Note that, with the three-dimensional structure of cells, if the respective hollow fibers 21 are removed at the stage where the respective cell clusters are still growing, the remaining space of the respective hollow fibers 21 can also be used for causing the adjacent cell clusters to grow and bond.

(3) Second Embodiment (3-1) Overall Configuration of Cell Culture System According to the Second Embodiment In the second embodiment, a mouse myoblast is used for forming the cell clusters relatively easily. Because the C2C12 cells have a natural fusion activity which forms muscle fibers upon differentiation, and it is expected that they will bond with each other prior to the differentiation induction.

In order to prepare the cell clusters, 100 [µl] of cell suspension ($10^4$ to $10^5$ [cells/ml] in DME/RPMI1640 1/1 to which 10[%] fetal bovine serum has been added) was placed in each of the wells of 96 well plates (MS-9096V; manufactured by Sumitomo Bakelite), and left to stand overnight. Consequently, the diameter of the primarily formed C2C12 spheroid changed between 100 to 400 [µm] in dependence of the initial cell mass in the suspension.

Figure 5:
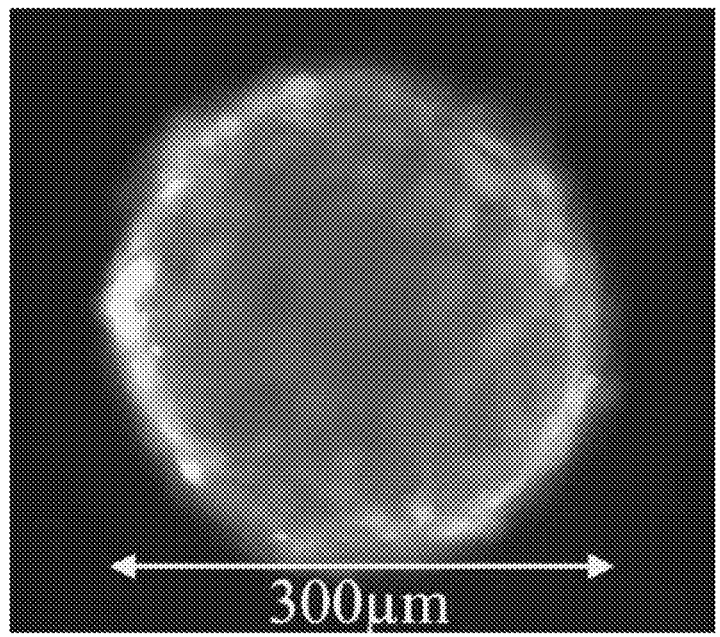
FIG. 5 is a diagram showing a fluorescently stained cell cluster (C2C12 spheroid) used in the second embodiment of the present invention.
Figure 6:
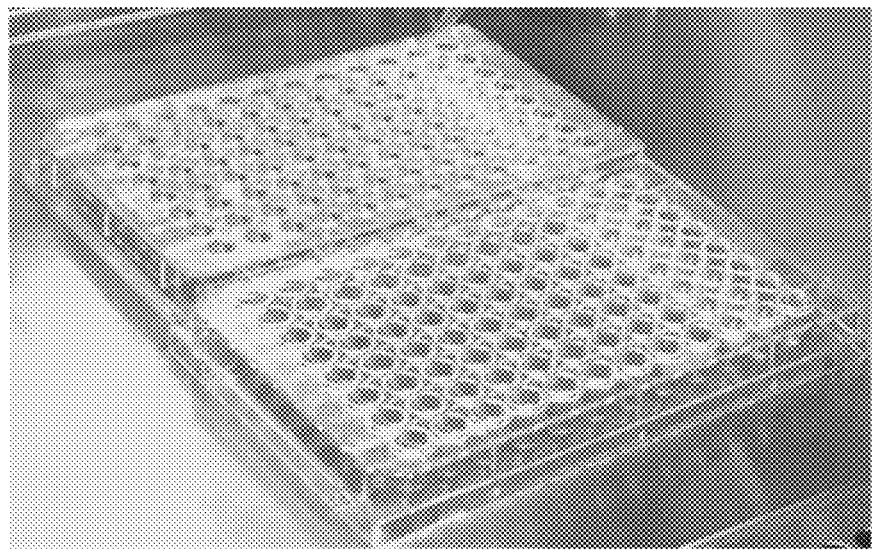
FIG. 6 is a diagram showing a state in which a plurality of cell clusters are formed on a multi-well plate.

In the present invention, cell clusters having a size of approximately 300 [µm] are used. A cell cluster of C2C12, which was fluorescently stained with Calcein AM to assure the cell survival rate, is shown in FIG. 5. Cell clusters are formed from cells in advance on the multi-well plate shown in FIG. 6, and disseminated to the cell culture system 100 (FIG. 7) described later.

Figure 7:
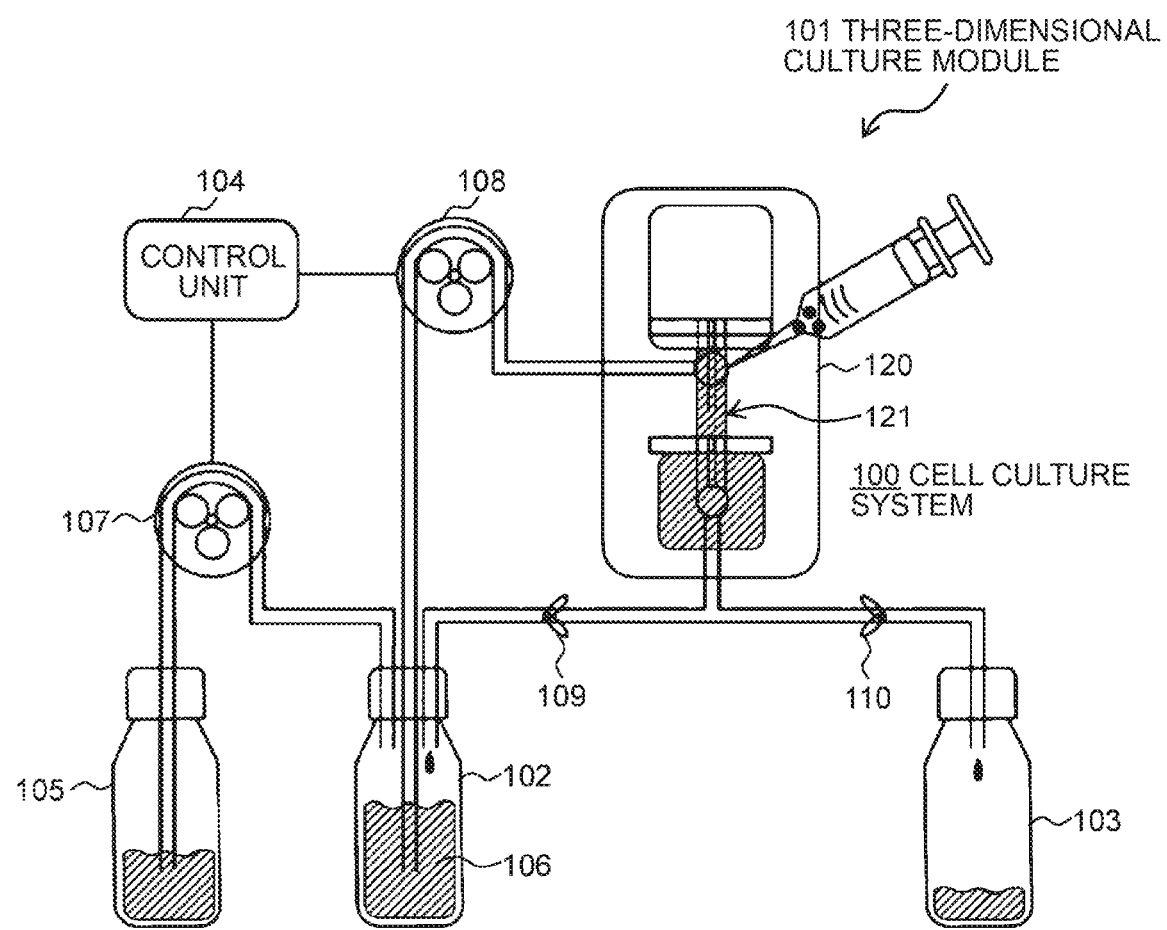
FIG. 7 is a schematic diagram showing an overall configuration of the cell culture system according to the second embodiment of the present invention.

As shown in FIG. 7, with the cell culture system 100 according to the second embodiment, a storage container 102 is connected to the upstream section and a recovery container 103 is connected to the downstream section of the three-dimensional culture module 101, and, under the integrated control of the control unit 104, a culture solution 106 supplied from a culture vessel 105 housing a fresh culture solution is perfused to a three-dimensional culture module 101 while maintaining a constant culture environment condition with the storage container 102 as a buffer.

With the cell culture system 100, under the control of the control unit 104, the culture solution 6 sucked from the culture vessel 105 with a supply pump 107 is once stored in the storage container 102, and thereafter supplied to the three-dimensional culture module 101 with a circulation pump 108.

A new culture solution 106 is continuously supplied from the storage container 102 to the three-dimensional culture module 101, and cell clusters are also sequentially supplied from the outside at a predetermined timing to the three-dimensional culture module 101. The three-dimensional culture module 101, as described later, forms a three-dimensional structure of cells by bonding a plurality of cell clusters while stacking them in a flow path direction under circumstances where the culture solution 106 is perfused from the culture vessel 105 to the recovery container 103 via the storage container 102.

The culture solution 106 discharged from the three-dimensional culture module 101 is transferred to the recovery container 103. The downstream section of the three-dimensional culture module 101 is connected to both the recovery container 103 and the storage container 102, and transfers the culture solution to one of the vessels 102, 103 according to the switching action of the respective stop valves 109, 110.

Note that, because the cells consume oxygen based on metabolic activity, it is important that the oxygen concentration in the culture solution is not lowered. Thus, by respectively connecting the culture vessel 105, the storage container 102, the three-dimensional culture module 101 and the recovery container 103 via a silicone tube (not shown), the culture solution 106 having a constant oxygen concentration and flowing in the silicone tube can be constantly supplied to the cell clusters because oxygen heads toward equilibrium with the outside air due to the high gas permeability of silicone rubber.

With the cell culture system 100, the liquid temperature and the concentration of carbon dioxide existing in a solution are controlled so that the culture solution 106 to be supplied to the three-dimensional culture module 101 becomes an optimal culture environment (physiological environment or similar environment) for cell culturing.

In other words, the control unit 104 uses a $CO_2$ gas cylinder (not shown) to inject carbon dioxide into, and cause the carbon dioxide to exist in, the culture solution 106 while sucking the culture solution 106 from the culture vessel 105 with the supply pump 107. Here, the control unit 104 controls the pH region of the culture solution 106 to be between 6.8 and 7.2 by maintaining the concentration of the carbon dioxide existing in the culture solution 106 at roughly 5% based on the detection result of a $CO_2$ sensor (not shown) positioned at the downstream section of the three-dimensional culture module 101.

Moreover, the control unit 104 controls a heater (not shown) so as to maintain the temperature of the culture solution 106 sucked from the culture vessel 105 at 37° C. based on the detection result of a temperature sensor (not shown) positioned at the downstream section of the three-dimensional culture module 101.

Furthermore, the control unit 104 drive-controls a circulation pump 108 so as to maintain the flow rate of the culture solution 106 supplied from the storage container 102 to the three-dimensional culture module 101 at an intended condition. The circulation pump 108 is subject to PWM (Pulse Width Modulation) control for variably controlling the flow rate. As the parameter values therefor, the volume of the storage container 102 is set to 100 [ml], the diameter of the silicone tube is set to 2 [mm], the diameter of the hollow fiber 130 (FIG. 8 and FIG. 9) is set to 0.5 [mm], and four hollow fibers 130. In order to satisfy the requirements of the circulation rate, the initial value of the discharge flow rate of the circulation pump 108 is set to 8 [ml/min].

With the cell culture system 100, as described above, it is possible to constantly supply and perfuse a new culture solution 106 to the three-dimensional culture module 101 from the culture vessel 105 in an environmental condition similar to a physiological environment.

With the cell culture system 100, in order to bond the cell clusters and generate tissues in the three-dimensional culture module 101, it is necessary to three-dimensionally house multiple cell clusters. Moreover, in consideration of the transplantation application after preparation, the structure enables dissemination, culture and tissue collection of cell clusters.

Moreover, with the cell culture system 100, in order to deal with the proliferation and growth of cells in the three-dimensional culture module 101, it is necessary to supply nutrition and oxygen at a broad rate fluctuation. Thus, the cell culture system 100 has a structure for controlling the circulation volume of the culture solution 106, discharging waste material from the cell clusters, and supplying fresh nutrition.

Furthermore, with the cell culture system 100, the occurrence of microbiological contamination (contamination) during cell culturing is the largest problem that is anticipated with the greatest frequency. When contamination occurs, the possibility of apoptosis (cell death) will increase due to deterioration in pH and nutrients of the culture solution. Thus, the cell culture system 100 has a structure, and is formed from a material, for preventing the occurrence of contamination in order to protect the cultured cells and assure the reliability of results.

(3-2) Configuration of Three-Dimensional Culture Module According to the Second Embodiment The cell culture system 100 according to the present invention has a structure not only capable of preventing contamination by causing the three-dimensional culture module 101 to have a sealed structure, but also capable of being easily and promptly disassembled for enabling the extraction of the cell clusters. In order to prevent contamination, while it is desirable to cause the flow path space in the three-dimensional culture module 101 to have a sealed structure, for example, if the flow path space including the hollow fibers is completely sealed using epoxy resin, the module itself needs to be cut open in order to extract the cell clusters after being cultured.

When considering the transplantation of the cultured cell tissues, it is necessary to develop a three-dimensional culture module which not only has a sealed structure, but which can be easily and promptly disassembled. Thus, in order to simultaneously pursue sealability and extraction of cultured tissues, proposed is a three-dimensional culture module 101 which uses a seal member such as an O-ring.

Figure 8:
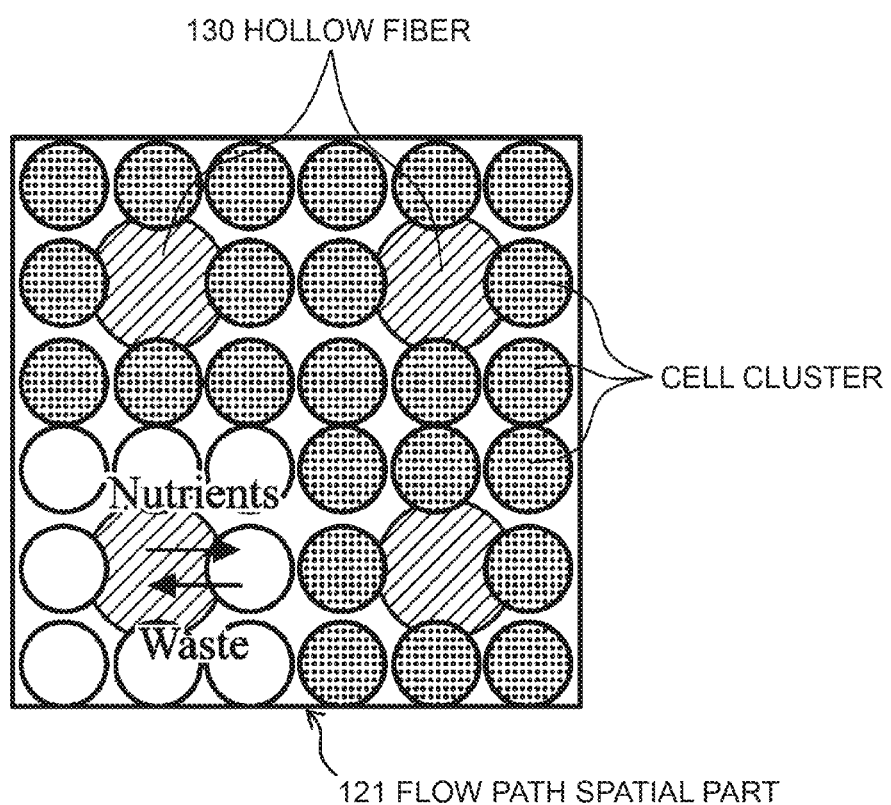
FIG. 8 is a schematic cross section of the flow path spatial part within the housing in the three-dimensional culture module according to the second embodiment.

As shown in FIG. 8, the three-dimensional culture module 101 is configured by forming a flow path spatial part 121, as a closed space, within a housing 120 (first case 120A and second case 120B) generally configured from a transparent member.

The flow path spatial part 121 is a closed space formed within a ring of an O-ring 122 by bonding a first case 120A and a second case 120B, in which grooves of a predetermined shape are formed on either or both of opposing surfaces, by interposing the O-ring 122 as an annular seal member so as to surround the grooves.

As characteristics of the O-ring 122, considered may be the point where the structure is simple and easy to remove, the point corresponding to a broad temperature range, and the point having a high sealing function against the fluid. Upon designing the vessel, a shape that can be tightened with O-ring fitting grooves and bolts BT1 to BT8 and nuts NT1 to NT8.

The material of the housing 120 (first case 120A and second case 120B) needs to be an optically transparent material and have heat resistance capable of withstanding heat treatment required for sterilization in order to observe the morphological change of cells and the existence of contamination.

Figure 9:
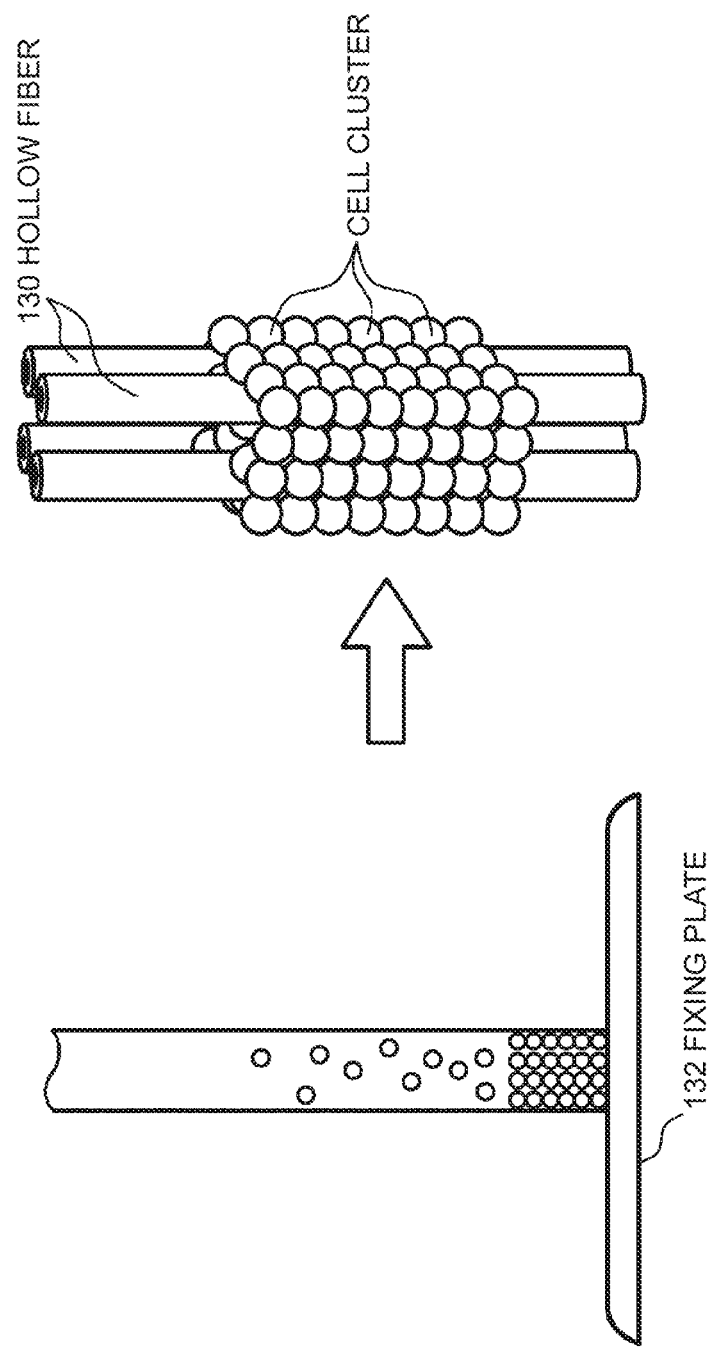
FIGS. 9A and -9B are a schematic diagrams for explaining a stacked state of the cell clusters in contact with the outer surface of a plurality of hollow fibers in the second embodiment.

Moreover, because the effect of sharing nutrition and oxygen of hollow fibers decreases in proportion to distance according to the diffusion rule of substances, it is important to place the hollow fibers inside the cultured tissues. Thus, as shown in FIG. 8 and FIG. 9(*a*), FIG. 9(*b*), the plurality of hollow fibers 130 and the plurality of cell clusters surrounding the respective hollow fibers 130 are placed at equal distance, and the flow path spatial part 121 is formed within the housing 120 so that the cell clusters can be stacked in the upward direction (fiber longitudinal direction).

In order to circulate the culture solution via the hollow fibers 130, it is necessary to provide a supply port and a discharge port of the culture solution 106 for connecting to the housing 120.

However, because the hollow fibers 130 are soft and easily bendable, if they undergo deflection in a state where the cell clusters are stacked, there is a possibility that a part of nutrition and oxygen may not be sufficiently supplied to the cells. Accordingly, by adopting a structure in which the hollow fibers 130 are placed in parallel to the stacking direction of the tissues, and tensile force is applied to either end, it is possible to realize a design for preventing the deflection of the hollow fibers 130.

Moreover, because the survival rate of cells will deteriorate under a condition where the distance from the hollow fibers 130 to the cell clusters is 500 [μm] or more, the hollow fibers 130 need to be placed so as to avoid necrosis. Thus, with the three-dimensional culture module 101 according to the present invention, the hollow fibers 130 are placed so that the maximum distance from the hollow fibers 130 will be approximately 300 [μm], and the width of the flow path spatial part (stack area) 121 in the housing 120 will be 2 [mm] (FIG. 8).

Moreover, in order to supply sufficient nutrition and oxygen according to the growth and proliferation of cells and eliminate waste material from cells, it is necessary to variably control the circulation rate of the culture solution 106 supplied to the three-dimensional culture module 101. In order to attain the optimal rate setting of the circulation pump 108, consideration needs to be given to the characteristics of the cell line, buffer capacity of the culture medium, and addition of serum, but when in the least the amount of supplied culture media per day is the amount of culture medium for 1 tank, it has been confirmed that the viable cell count and the survival rate of culturing considerably improve.

Moreover, the upper limit of the circulation rate is restricted by the low/high of sensitivity relative to the physical shear stress of the cultured cell line. The physical shear stress subject by mammalian cells upon performing prefusion culture using the hollow fibers 130 has been evaluated, and, if the shear rate is 3000 [1/sec] or less, the cell survival rate will not deteriorate.

The size S of the shear rate is represented as shown in formula (1) below when the flow rate is Q, the radius of the hollow fiber 130 is r, the average of the flow rate is $V_{av}$, and the diameter of the hollow fiber 130 is D.

[Math 1]
$$S = \frac{4Q}{\pi r^3} = \frac{8V_{av}}{D} \quad (1)$$

Here, when N-number of hollow fibers 130 are used, the average $V_{av}$ of the flow rate is represented as shown in formula (2) below.

[Math 2]
$$V_{av} = \frac{4Q}{\pi D^2 N} \quad (2)$$

Formula (3) below is derived from foregoing formula (1) and formula (2).

[Math 3]
$$S = \frac{1.7 \times 10^5 Q}{D^3 N} \quad (3)$$

By using the foregoing results, with the cell culture system 100, the circulation rate needs to be determined so that the shear rate S subject by cells is 3000 [1/sec] or less, and so that the amount of supplied culture media becomes equal to or greater than the amount of culture medium for 1 tank.

Figure 10:
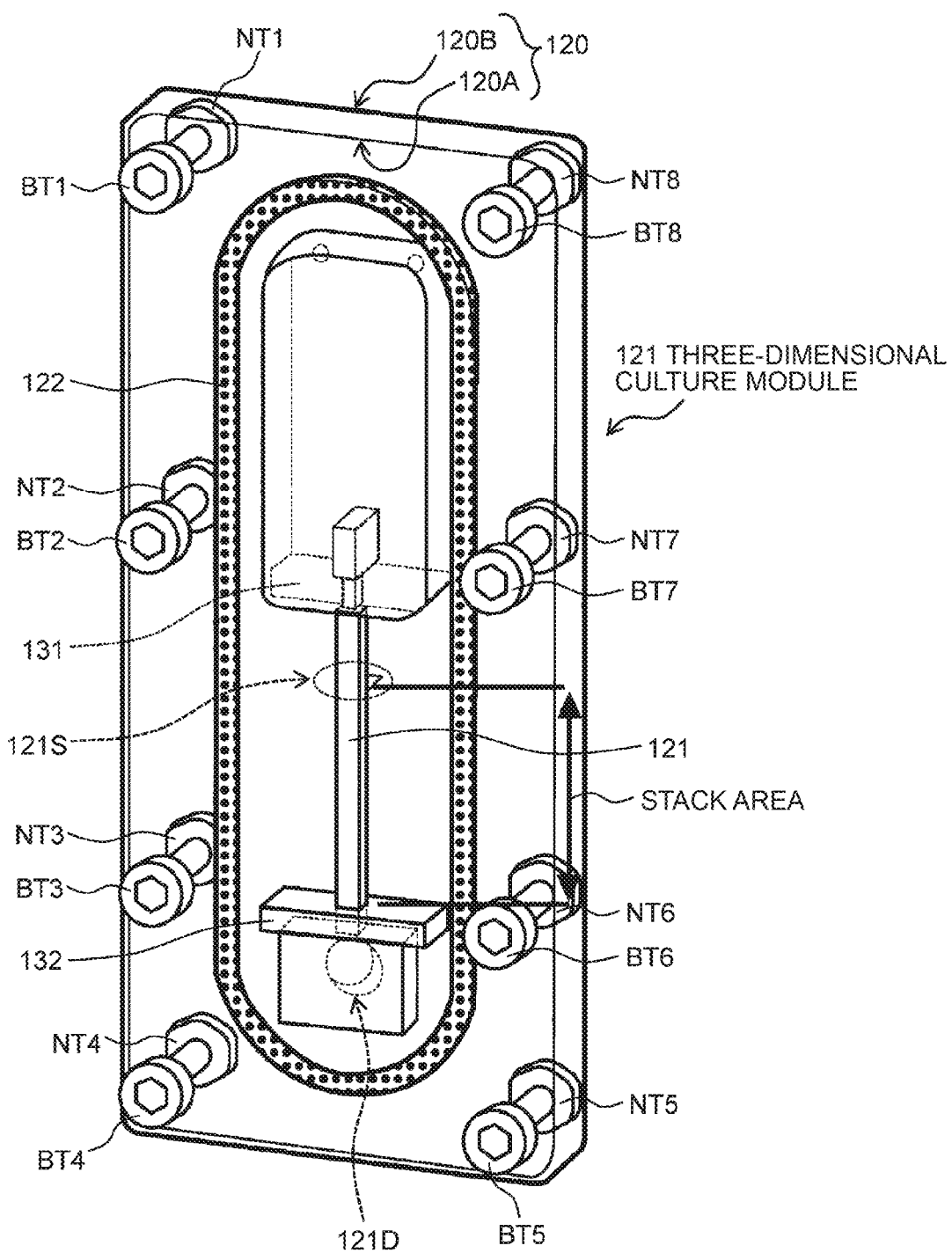
FIG. 10 is a perspective view showing the configuration of the three-dimensional culture module according to the second embodiment.

Furthermore, with the three-dimensional culture module 101, as shown in FIG. 10, the flow path spatial part 121 formed in the housing 120 (first case 120A and second case 120B) includes a supply port 121S for connecting to the storage container 102 via the silicone tube, and a discharge port 121D for connecting to the recovery container 103 via the silicone tube, and the cell clusters can be disseminated via the supply port 121S.

Moreover, the flow path spatial part 121 in the housing 120 can be sealed based on the tightening with the O-ring 122 and the bolts BT1 to BT8 and the nuts NT1 to NT8, and the cell clusters inside can be immediately removed by loosening the tightening of the bolts BT1 to BT8. A transparent polycarbonate plate is used as the material of the housing 120 (first case 120A and second case 120B), which has high heat resistance and transparency, and enables the application of autoclave sterilization and internal observation.

Figure 11:
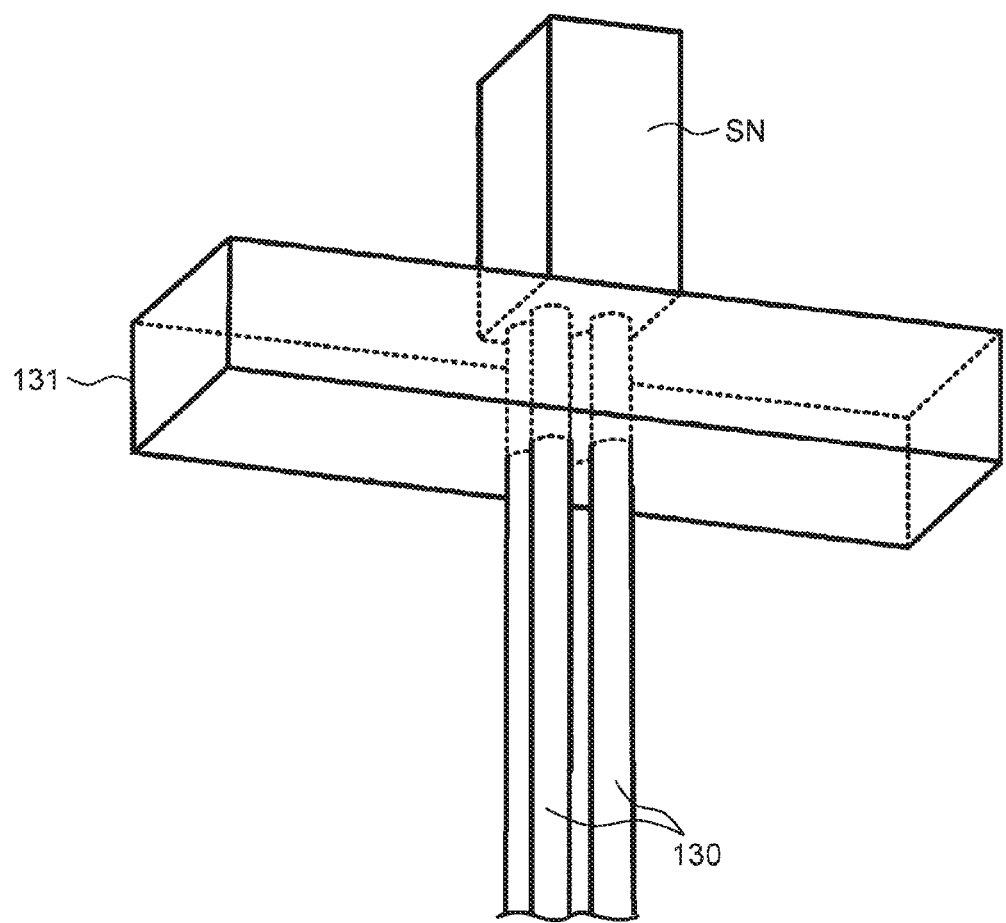
FIG. 11 is a schematic diagram for explaining the parallel positional accuracy assurance of a plurality of hollow fibers according to the second embodiment.

Four hollow fibers 130 made from polysulfone having a diameter of 0.5 [mm] and a pore size of 0.1 [μm] were used. The two fixing plates 131, 132 have penetration holes having a diameter of 0.6 [mm] at equally spaced intervals, and parallel positional accuracy can be assured by passing the hollow fibers 130 through both plates 131, 132 (FIG. 11).

When the two fixing plates 131, 132 are fitted into the upper and lower space of the flow path spatial part 121 to hold the plurality of hollow fibers 130, the length is set so that subtle tensile force is applied to either end of each of the hollow fibers 130, and either end is fixed with silicone SN to prevent the occurrence of deflection.

Figure 12:
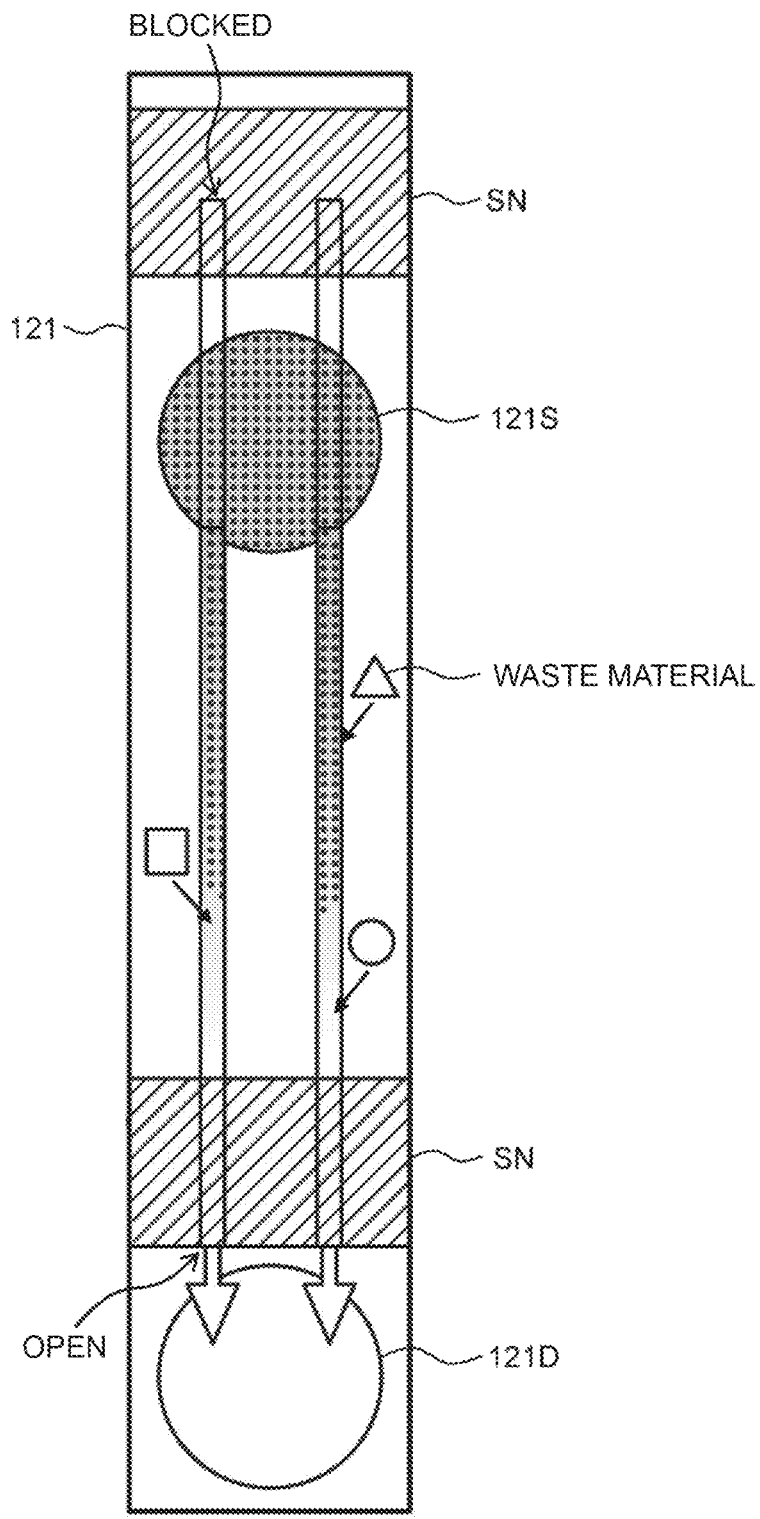
FIG. 12 is a conceptual diagram showing the configuration of causing only one end of a plurality of hollow fibers to be a negative pressure according to the second embodiment.

Moreover, as shown in FIG. 12, by blocking one side with silicone SN and opening the other side of each end of the plurality of hollow fibers 130, because the end of the discharge side becomes a negative pressure when the culture solution 106 enters from the supply port 121S, metabolic substance (waste material) in the culture solution 106 can be discharged to the discharge port 121D.

By disseminating the cell clusters to the three-dimensional culture module 101, the cell clusters are stacked as shown in FIG. 9(a) and FIG. 9(b) described above, and tissues can thereby be formed.

Note that, in the cell culture system 100, all components configuring the control unit 104 are structured so that they do not contact the outside air by being sealed in a waterproof box (not shown) of the protection standard IP67. By sanitizing the overall outer surface of the box with alcohol after mounting the box cover, the risk of contamination caused by electrical components, which cannot be subject to autoclave sterilization, can be reduced. All components other than the control unit 104 can be subject to high-pressure steam sterilization in an autoclave (sterilization of 20 minutes at 121[° C.] where the saturated steam pressure of water normally becomes 2 atm). All cables connected to the control unit 104 are connected to the outside and inside of the control unit 104 via the IP68 waterproof cable connector, and it is thereby possible to supply the power and drive the actuator while maintaining sealability.

Based on the guidelines of sterilization assurance in the medical front, the evaluation items of cleanliness and drying (Item 1), physical compatibility (Item 2), and permeability (Item 3) are confirmed. With regard to Item 1, all appliances that were used were new and sufficiently cleaned and dried. With regard to Item 2, at the time of material selection, a material having a temperature limit that is higher than the highest temperature of the autoclave, which is 121[° C.], was used, and it was confirmed that no deformation, rupture and melting occurred before or after the autoclave sterilization with regard to changes in the temperature and the pressure.

With regard to Item 3, the components that come into contact with the culture solution 106 were subject to autoclave sterilization in a state of being connected with the silicone tube. Silicone rubber is significantly characterized in having particularly high permeability of steam in gas permeation, and it is possible to cause all components, which have been connected, to permeate steam in an extremely efficient manner while realizing a closed system in which bacteria or the like cannot enter.

Figure 13:
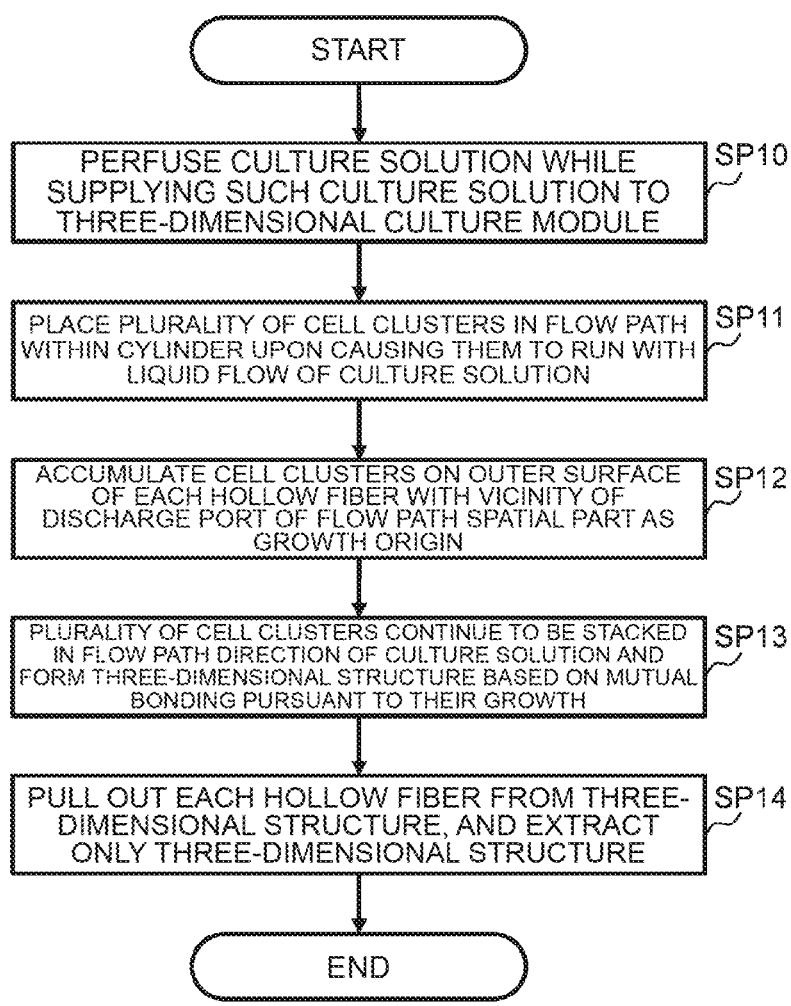
FIG. 13 is a flowchart showing an operational example of the cell culture system according to the second embodiment.

(3-3) Three-Dimensional Structuring Method of Cells According to the Second Embodiment FIG. 13 shows a flowchart showing an operational example of the cell culture system 100 according to the second embodiment. Foremost, in the three-dimensional culture module 101, the plurality of hollow fibers 130 that are fixed and held between two fixing plates 131, 132 are housed in the flow path spatial part 121 of the housing 120.

In other words, after the plurality of hollow fibers 130 are fitted into the upper and lower space of the flow path spatial part 121 together with the two fixing plates 131, 132, they can be housed in a closed space formed within the ring of an O-ring 122 by bonding a first case 120A and a second case 120B via the O-ring 122.

Next, in the cell culture system 100, the control unit 104 controls the supply pump 107 and the circulation pump 108 and perfuses the culture solution 106 in the culture vessel 105 while supplying the culture solution 6 from a supply port 121S of the flow path spatial part 121 in the housing 120 of the three-dimensional culture module 101 and maintaining a constant culture environment condition (step SP10).

In a state where a new culture solution 106 is constantly supplied from the storage container 102 to the flow path spatial part 121, a plurality of cell clusters are placed in the flow path from the supply port 121S of the flow path spatial part 121 upon causing the cell clusters to run with the liquid flow of the culture solution 106 at the intended timing (step SP11).

The plurality of cell clusters placed within the flow path spatial part 121 start accumulating on the outer surface of each hollow fiber 130 while randomly coming into contact with the surface of the fixing plate 132 near the discharge port 121D (step SP12). Next, when the plurality of cell clusters are further placed within the flow path spatial part 121 upon running with the liquid flow of the culture solution 610, they are accumulated on the outer surface of each of the hollow fibers 130 while coming into contact with the previously accumulated cell clusters, and continue to become stacked in the flow path direction.

Here, growth factors or nutritional factors are supplied to the respective cell clusters, which are accumulated on the outer surface, from the hollow interior of each hollow fiber 130 via multiple ultrafine pores, and at the same time metabolic substance and waste material are filtered and discharged to the hollow interior from each of the cell clusters via the multiple ultrafine pores.

Accordingly, in the three-dimensional culture module 101, not only do the adjacent cell clusters grow and bond with each other while a plurality of cell clusters accumulate on the outer surface of each of the hollow fibers 130, the cell clusters stacked along the flow path direction also grow and bond with each other (step SP13).

When the placement of cell clusters in the three-dimensional culture module 101 is eventually completed, a three-dimensional structure in which multiple cell clusters are mutually bonded in a three-dimensional direction is formed in the flow path spatial part 121 of the housing 121 with the vicinity of the discharge port 121D as the growth origin.

In the three-dimensional culture module 101, after the plurality of hollow fibers 21 are removed from the flow path spatial part 121 of the housing 120 together with the two fixing plates 131, 132, by removing all hollow fibers 130 from the fixing plates 131, 132 in the push-pull operation (reciprocating motion in the fiber direction), the three-dimensional structure of cells can thereby be extracted (step SP14).

Note that, with the three-dimensional structure of cells, if the respective hollow fibers 130 are removed at the stage where the respective cell clusters are still growing, the remaining space of the respective hollow fibers 130 can also be used for causing the adjacent cell clusters to grow and bond.

(3-4) Experimental Results According to the Second Embodiment

With the cell culture system 100, as a preliminary step of performing cell culturing, the existence of contamination is confirmed upon continuously circulating the culture solution for verifying whether the cells can be applied safely.

With the cell culture system 100, only the culture solution 106 was circulated for 5 days in a state of not containing any cells between the storage container 102 and the three-dimensional culture module 101. The experiment was conducted within a $CO_2$ incubator as an actual cell culture environment (room temperature 37° C., $CO_2$ concentration 5%, humidity >95%). All experimental operations were all performed within a clean bench, which is a sterile environment. As the detection method of contamination, the following items were confirmed every 24 hours.

As Item 1, whether the color of the culture solution 106 changes from red to yellow was confirmed. As Item 2, whether the level of turbidity of the culture solution 106 appears to be milky white was confirmed. As Item 3, whether the motion of bacterial can be observed was confirmed based on observation using a microscope. Upon confirming the phase difference with a microscope, a small amount of culture solution was extracted from the recovery container 103 and transferred to a dish for observation.

Figure 15A:
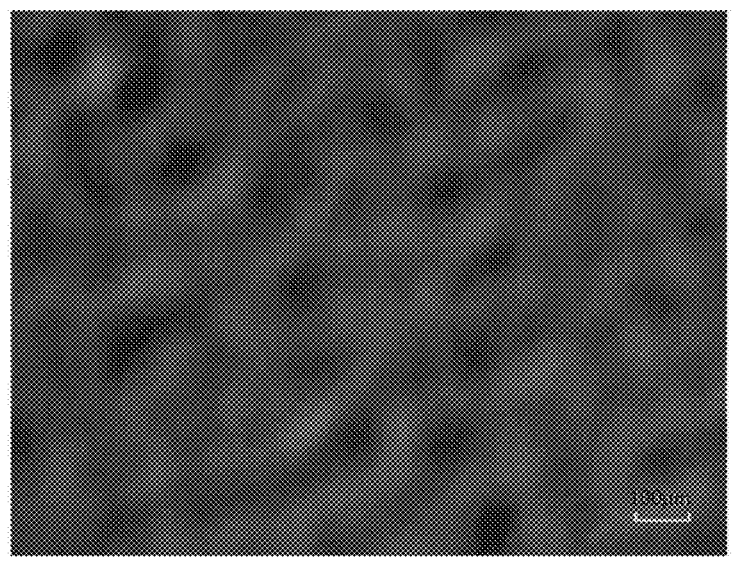
FIGS. 15A and 15B are diagrams showing the results before and after the test on the existence of motile bacteria in the second embodiment.
Figure 15B:
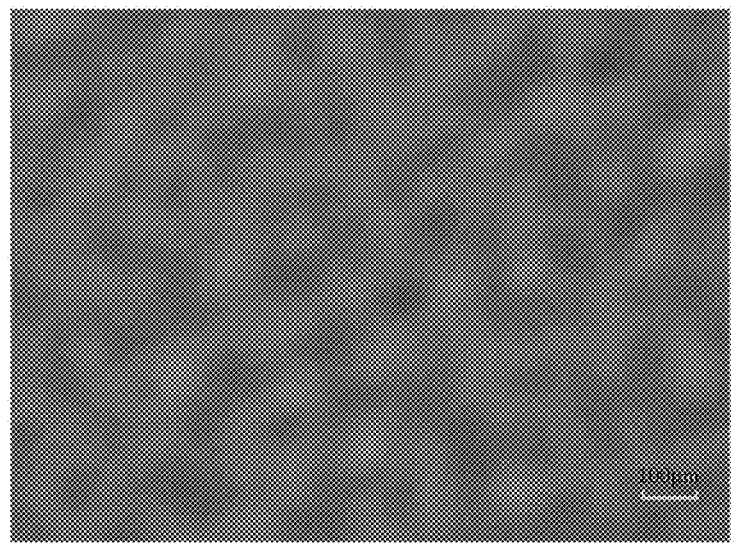

As the foregoing experimental results, the color of the culture medium has not changed before or after the experiments based on FIG. 14(a) and FIG. 14(b) as the observations before and after the experiments (before and after the lapse of 120 minutes) in the contamination test, and it was confirmed that the culture solution 106 is not turbid. Moreover, based on FIG. 15(a) and FIG. 15(b), it was confirmed that there was no motile bacteria before or after the experiment.

Next, whether the intended stacking of cell clusters and cell growth are observed was confirmed upon disseminating the cell clusters in the cell culture system 100. As the culture solution 106 to be circulated, 50 [ml] of DMEM (Gibco)+ 10% FBS was used. The prepared C2C12 spheroids were sucked with the circulation pump 108 and separated from the fixing plate 132. The sucked cell clusters were stored in the silicone tube. Because all cultured cells can be beneficially used, whether there is any cell cluster remaining in the wells of the fixing plate 132 was confirmed with a microscope.

A silicone tube was connected to the supply port 121S of the flow path spatial part 121 of the three-dimensional culture module 101, and the cell clusters in the silicone tube were disseminated to the flow path spatial part 121 by rotating the circulation pump 108 in reverse. Subsequently, the cell culture system 100 was placed in an incubator (not shown), and the circulation of the culture solution 106 was started. The inside of the three-dimensional culture module 101 was confirmed with a microscope after 24 hours.

Figure 17A:
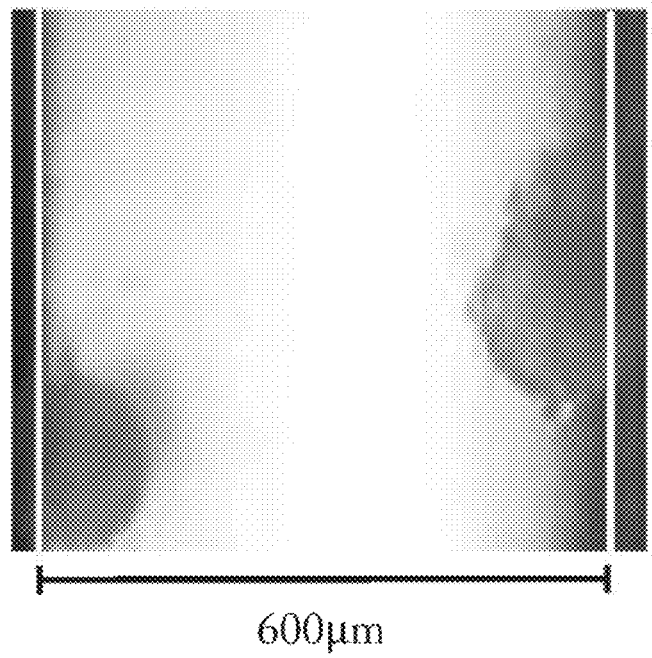
FIGS. 17A and 17B are is a partially enlarged views regarding the condition between the hollow fibers in FIG. 16.
Figure 17B:
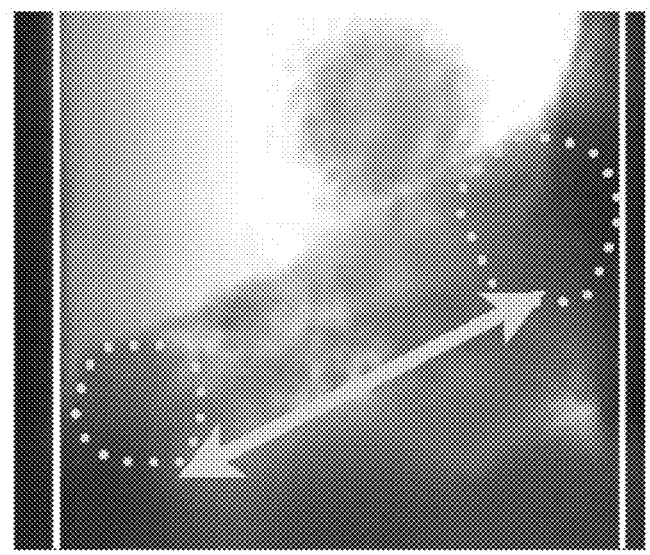

FIG. 16(a) and FIG. 16(b) show the observations of the inside of the three-dimensional culture module 101 after 24 hours of the foregoing cell cluster dissemination experiment. The black part is the hollow fiber 130, and the cell clusters are encompassed with a white dotted line. FIG. 17, which is an enlarged view of the middle section of FIG. 16(b), shows the changes at the time of starting the experiment (FIG. 17(a)) and after the lapse of 24 hours (FIG. 17(b)). Based on FIG. 16(b), it is possible to confirm that the cell clusters are stacked in the overall flow path spatial part 121. Moreover, based on FIG. 17(b), it is possible to confirm that the cell clusters are growing and partially fusing, and that the shape has deformed from a spherical shape.

(5) Other Embodiments

While the first embodiment explained a case of the three-dimensional culture module 2 forming a three-dimensional structure of a substantially cylindrical shape by bonding a cell cluster group on the outer surface 21A of a plurality of linear hollow fibers 21 in a three-dimensional direction pursuant to its growth with the flat plate 22 as the growth origin, the present invention is not limited thereto, and the shape and bent state of the plurality of hollow fibers may be freely designed to match the intended three-dimensional shape.

Note that the cylinder 20, which is a cylindrical part, restricts the outer wall of the three-dimensional structure of cells, and is not a mold that guides the shape of the three-dimensional structure. With the three-dimensional structure of cells, the overall size and shape are identified in the three-dimensional direction as a result of the mutually adjacent cell clusters growing and bonding, while accumulating on the outer surface 21A of each of the hollow fibers 21 and also becoming stacked in the flow path direction.

For example, with the plurality of hollow fibers 21 sandwiched between the flat plate 22 and the through-type holding plate 23, by forming the center part of the flow path of the culture solution 6 in a linear shape, and forming them in a curved shape so as to protrude externally as they head outward, the formed three-dimensional structure of cells can be formed into an organ shape in which the center is swelled.

Figure 18A:
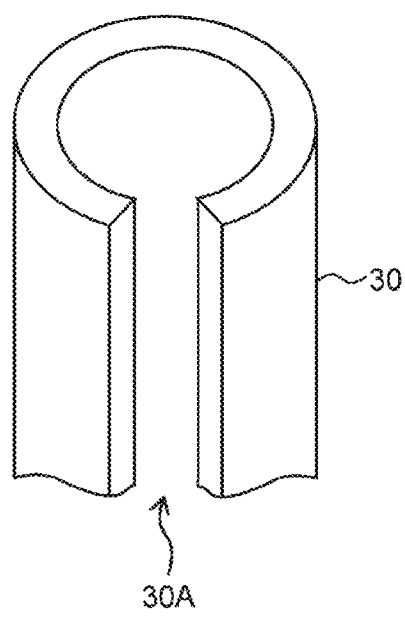
FIGS. 18A and 18B are a schematic diagram diagrams showing the configuration of a fiber according to another embodiment.
Figure 18B:
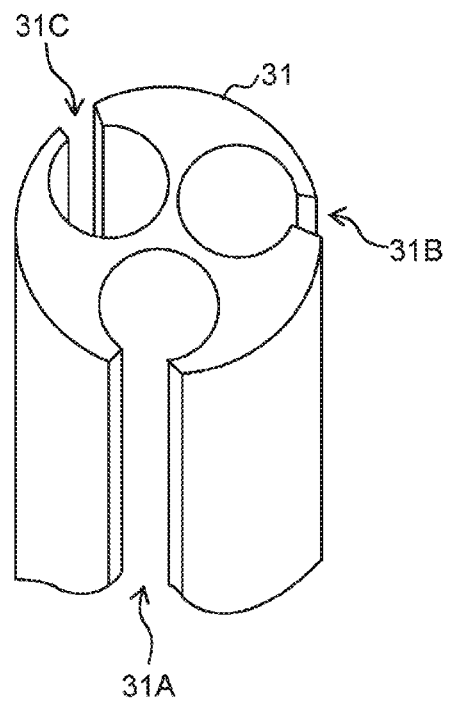

Moreover, while the first embodiment explained a case of applying hollow fibers 21 having a hollow interior formed from a filamentous hollow fiber membrane as the plurality of fibers configuring the three-dimensional culture module 2, the present invention is not limited to a hollow structure, for instance, as shown in FIG. 18(A) and FIG. 18(B), fibers with lateral grooves formed along a longitudinal direction may also be applied. FIG. 18(A) shows a case of forming a single groove 30A in one fiber 30, and FIG. 18(B) shows a case of forming three grooves 31A to 31C in one fiber 31. These fibers 30, 31 have multiple slit-like ultrafine pores on the wall surface part other than the lateral grooves, and it will suffice so as long as matter exchange can be performed between the lateral groove interior and the internal space of the cylinder 20 via the respective ultrafine pores.

Each of the foregoing hollow fibers 21 is not limited to a linear shape, and the hollow fibers 21 may be freely designed to have the intended shape and the intended size, by bending or curving the hollow fibers 21, so as long as their cross section shape has a hollow or a lateral groove which enables the cell clusters, which are accumulated on the outer surface, to be pulled out without being damaged. If the cylinder 20 is the flow path of the culture solution 6, the cross section shape and size of the cylinder 20 may also be freely designed so as long as the culture solution 6 can be perfused without obstructing the insertion of the flat plate 22.

Moreover, while the first embodiment explained a case of maintaining the temperature and carbon dioxide concentration of the culture solution 6 to be an environmental condition close to a physiological environment by the control unit 5 of the cell culture system 1 controlling the pump 7 and the $CO_2$ gas cylinder 8 based on the temperature of the temperature and carbon dioxide concentration of the culture solution 6 obtained from the temperature sensor 11 and the $CO_2$ sensor 12, the present invention is not limited thereto, and control may also be performed by additionally detecting the oxygen concentration and the nitrogen concentration.

Furthermore, while the first embodiment explained a case of placing a plurality of cell clusters in the flow path from the open end 20A of the cylinder 20 upon causing the cell clusters to run on the liquid flow of the culture solution that the intended timing, the present invention is not limited thereto, and automation may be sought by additionally providing a cell placement adjustment unit (not shown) for adjusting the number of cell clusters to be placed in the flow path of the cylinder 20, and the placement timing thereof, in accordance with the control state of the culture solution 6 controlled by the control unit 5.

Furthermore, while the first embodiment and the second embodiment did not particularly limit the growth factors and nutritional factors contained in the culture solution 6, 106, for instance, epidermal growth factors (EGF), fibroblast growth factors (FGF), platelet-derived growth factors (PDGF), hepatocyte growth factors (HGF), transforming growth factors (TGF), neurotrophic growth factors (NGF), vascular endothelial growth factors (VEGF) and insulin-like growth factors (IGF) may be considered. Other growth factors and nutritional factors may also be used according to the type of cell clusters to be cultured.

While the second embodiment explained a case of the three-dimensional culture module 101 forming a three-dimensional structure of a substantially cylindrical shape by bonding a cell cluster group on the outer surface of four linear hollow fibers 130 in a three-dimensional direction pursuant to its growth with the fixing plate 132 in the vicinity of the discharge port 121D of the flow path spatial part 121 as the growth origin, the present invention is not limited thereto, and, so as long as it is in the vicinity of the discharge port 121D, any position where they can become the naturally come into close contact on the flow path, without having to come into contact with the surface of the fixing plate 132, can be used as the growth origin.

Furthermore, while the second embodiment explained a case of fixing the plurality of hollow fibers 130 in the flow path spatial part 121, the present invention is not limited thereto, and it is possible to further comprise a vibration application part (not shown) which alternately applies subtle vibration to each of the fibers in a flow path direction or a reverse direction in accordance with a growth process of each of the cell clusters under control of the control unit. It is thereby possible to prevent each cell cluster which is contacting the outer surface of each of the hollow fibers 130 from entering each micropore formed in the hollow fibers 130 and making it difficult to slide in the flow path direction. It is thereby possible to remove the grown cell clusters from the hollow fibers 130 relatively easily.

REFERENCE SIGNS LIST 1, 100 . . . cell culture system, 2, 101 . . . three-dimensional culture module, 3, 105 . . . culture vessel, 4, 103 . . . recovery container, 5, 104 . . . control unit, 6, 106 . . . culture solution, 7 . . . pump, 8 . . . $CO_2$ gas cylinder, 9 . . . heater, 10 . . . flow rate sensor, 11 . . . temperature sensor, 12 . . . $CO_2$ sensor, 20 . . . cylinder, 20A . . . open end, 20B . . . inner wall surface, 20C . . . groove, 21 . . . hollow fiber, 21A . . . fiber surface, 21H . . . ultrafine pores, 22 . . . flat plate, 23 . . . through-type holding plate, 30, 31 . . . fiber, 102 . . . storage container, 107 . . . supply pump, 108 . . . circulation pump, 120 . . . housing, 120A . . . first case, 120B . . . second case, 121 . . . flow path spatial part, 121S . . . supply port, 121D . . . discharge port, 122 . . . O-ring, 130 . . . hollow fiber, 131, 132 . . . fixing plate.

The invention claimed is:

1. A three-dimensional culture method of cells, comprising:
   positioning a plurality of fibers in a flow path spatial part, the flow path includes a space surrounded by an inner wall surface from a supply port to a discharge port of a culture solution, so that a longitudinal direction of each of the fibers is along a direction of the flow path while a predetermined interval is mutually maintained between the fibers;
   continuously supplying a culture solution to the flow path through the supply port;
   placing a plurality of cell clusters in the flow path at predetermined timing, and causing the cell clusters to run with a liquid flow of the culture solution being supplied in the flow path from the supply port;
   stacking the cell clusters on an outer surface of each of the plurality of fibers;
   culturing each of the cell clusters;
   controlling a flow rate of the culture solution being supplied into the flow path;
   adjusting a number of the cell clusters being placed in the flow path; and
   adjusting a placement timing of the cell clusters into the flow path,
   wherein a flat plate is provided in a downstream section of the flow path spatial part for serving as a growth support for the cell clusters being cultured in the flow path.

2. The three-dimensional culture method of cells according to claim 1, wherein each of the plurality fibers has a hollow or a lateral groove along a longitudinal direction formed therein, has a plurality of micropores that penetrate from an outer surface to a hollow interior or a lateral groove interior, and metabolic waste is removed from each of the cell clusters through each of the micropores.

3. The three-dimensional culture method of cells according to claim 2, wherein each of the plurality fibers supplies either or both of growth factors and nutritional factors to each of the cell clusters through each of the micropores.

4. The three-dimensional culture method of cells according to claim 1, wherein at least one or more among a temperature, a carbon dioxide concentration, an oxygen concentration and a nitrogen concentration of the culture solution are controlled.

5. The three-dimensional culture method of cells according to claim 1, wherein vibration is applied to each of the plurality fibers, along the flow path direction, at a predetermined timing in accordance with a growth process of each of the cell clusters.

* * * * *